United States Patent
Kutsanyan et al.

(10) Patent No.: US 10,098,920 B2
(45) Date of Patent: Oct. 16, 2018

(54) METHOD FOR PRODUCING A COMPLEX OF BIOLOGICALLY ACTIVE SUBSTANCES EXHIBITING HYPOGLYCEMIC ACTIVITY

(71) Applicant: Akop Surikovych Kutsanyan, Kharkiv (UA)

(72) Inventors: Akop Surikovych Kutsanyan, Kharkiv (UA); Vasyl Ivanovych Lytvynenko, Kharkiv (UA)

( * ) Notice: Subject to any disclaimer, the term of this patent is extended or adjusted under 35 U.S.C. 154(b) by 0 days.

(21) Appl. No.: 15/543,577

(22) PCT Filed: Jan. 14, 2015

(86) PCT No.: PCT/UA2015/000002
§ 371 (c)(1),
(2) Date: Jul. 14, 2017

(87) PCT Pub. No.: WO2016/114740
PCT Pub. Date: Jul. 21, 2016

(65) Prior Publication Data
US 2018/0008658 A1 Jan. 11, 2018

(51) Int. Cl.
*A61K 36/48* (2006.01)
*A61K 36/28* (2006.01)

(52) U.S. Cl.
CPC ............. *A61K 36/48* (2013.01); *A61K 36/28* (2013.01); *A61K 2236/00* (2013.01)

(58) Field of Classification Search
None
See application file for complete search history.

(56) References Cited

U.S. PATENT DOCUMENTS

2009/0093397 A1* 4/2009 Berlanda ............... A61K 36/48 514/1.1
2011/0281956 A1* 11/2011 Park ...................... A61K 36/53 514/731

FOREIGN PATENT DOCUMENTS

| RU | 2131740 C1 | 6/1999 |
| RU | 2002103852 A | 10/2003 |
| RU | 2284829 C2 | 10/2006 |
| RU | 2480231 C2 | 4/2013 |
| UA | 7005 C1 | 3/1995 |
| UA | 48031 C1 | 8/2002 |
| WO | 2007071333 A2 | 6/2007 |

OTHER PUBLICATIONS

Ayat Kaeidi et al: "Satureja khuzestanica attenuates apoptosis in hyperglycemic PC12 cells and spinal cord of diabetic rats", Journal of Natural Medicines, vol. 67, No. 1, Jan. 1, 2013 (Jan. 1, 2013), pp. 61-69, XP055197786, ISSN: 1340-3443, DOI: 10.1007/si1418-012-0646-y, p. 62, left-hand column, paragraph 6, right-hand column, paragraph 2, abstract.
Database WPI Week 201259, Thomson Scientific, London, GB; AN 2012-L64672, XP002741404.
Axel Helmstadter: "Beans and Diabetes: Phaseolus vulgaris Preparations as Antihyperglycemic Agents", Journal of Medicinal Food, vol. 13, No. 2, Apr. 1, 2010 (Apr. 1, 2010), pp. 251-254, XP055197906, ISSN: 1096-620X, DOI: 10.1089/jmf.2009.0002, the whole document.
Sanaz Vosough-Ghanbari et al: "Effects of Satureja khuzestanica on Serum Glucose, Lipids and Markers of Oxidative Stress in Patients with Type 2 Diabetes Mellitus: A Double-Blind Randomized Controlled Trial", Evidence-Based Complementary and Alternative Medicine, vol. 7, No. 4, Jan. 1, 2010 (Jan. 1, 2010), pp. 465-470, XP055197892, ISSN: 1741-427X, DOI: 10.1093/ecam/nenO18, the whole document.
Em Khorasgani et al: "*Satureja hortensis* L. Alcoholic Extract Ameliorates Cadmium—Induced Pancreatic Damage in Rats.", Middle-East Journal of Scientific Research, vol. 15, No. 1, Jan. 1, 2013 (Jan. 1, 2013), pp. 32-35, XP002741405, ISSN: 1990-9233, DOI: 10.5829/idosi.mejsr.2013.15.1.302, the whole document.
International Search Report for PCT/UA2015/000002, the whole document.

* cited by examiner

*Primary Examiner* — Michael Barker

(57) ABSTRACT

The invention relates to medicine and chemical and pharmaceutical industry, in particular, to methods for producing a complex of biologically active substances exhibiting hypoglycaemic activity of plant material. A method for producing a complex of biologically active substances exhibiting hypoglycaemic activity comprises extracting bean herb with alcohol followed by concentrating and/or drying the extract, wherein the extraction is carried out with 96% alcohol resulting in a first extract and a bean herb residue, wherein the first extract is concentrated resulting in a first solid extract or it is concentrated and dried resulting in a first dry extract and the bean herb residue is extracted with 70% alcohol resulting in a second extract at least a portion of which being concentrated resulting in a second solid extract or being concentrated and dried resulting in a second dry extract.

5 Claims, No Drawings

METHOD FOR PRODUCING A COMPLEX OF BIOLOGICALLY ACTIVE SUBSTANCES EXHIBITING HYPOGLYCEMIC ACTIVITY

FIELD OF THE INVENTION

The invention relates to medicine and chemical and pharmaceutical industry, in particular, to methods for producing a complex of biologically active substances exhibiting hypoglycaemic activity of plant material.

BACKGROUND OF THE INVENTION

Diabetes mellitus is one of the gravest medical and social problems, as it continuously spreads among all population segments, and complications associated with its progression represent a threat to a patient's life (blindness, kidney failure, diabetic gangrene of the extremities, myocardial infarction, apoplexy, etc).

According to the opinion of World Health Organization experts diabetes mellitus currently is a problem of all ages and countries, ranking third among the direct causes of death after cardiovascular diseases and cancer. At the moment there are about 110-120 million diabetics on our planet. Presumably, in 12-15 years the number will double.

Diabetes mellitus is a group of metabolic disorders characterized by hyperglycaemia which results from defects in insulin secretion, insulin action or a combination thereof. The most prevalent is non-insulin dependent diabetes (type II diabetes mellitus) caused by the violation of insulin secretion or the mechanisms of its interaction with tissue cells.

Numerous researches worldwide are focused on finding effective ways of the treatment for diabetes. It is proved that for every percentage point of glycated haemoglobin decrease the risk of the development of microvascular complications (retinopathy, nephropathy) is reduced by 35%. In addition, glycaemic control, along with the blood pressure normalization significantly reduces the risk of the development of coronary heart disease, cerebrovascular disease, and peripheral arterial disease in patients suffering from type II diabetes. Proceeding from this, the main goal of the treatment of the disease is to provide the most possibly complete recovery from carbohydrate metabolism, which can be achieved through creating and applying new and safe medicines, in particular of plant material, and through the technologies for manufacturing thereof.

It was found by the folk medicine and the research of scientists and experts in the search and selection of promising plants for producing hypoglycaemic activity substances, that some of the legume family members possess properties exactly like these. In particular, it is due to essential amino acids including arginine present in the fruit pods. Experimental and clinical studies have shown that extracts of the bean fruit pods reduce the amount of sugar in blood. It is methods for preparing biologically active substances that are of crucial importance to create effective diabetes treatment and prevention means of this plant material.

A method for producing an anti-diabetic agent of a fine cut mixture of dry plants, including bean pods is described in the Russian Federation patent 2131740 for an invention (publ. Jun. 20, 1999) and comprises the steps of: pouring 10 g of plant material with 400 ml of boiling water in an enamel vessel and conditioning in a water bath for 20 minutes, cooling the resulting infusion at room temperature for at least 45 minutes and filtering it through a cheesecloth, dividing the prepared infusion into 3 equal portions and taking one portion 3 times a day 30 minutes before taking meals in the course of 20-30 days.

A method for producing an anti-diabetic tea, comprising a plant material mixture, including bean pods is described in the Russian Federation patent 2284829 for an invention (publ. Oct. 10, 2006) and comprises the steps of: feeding fine cut and sieved material into a mixer, mixing it thoroughly and packing into 2 g paper filter bags. To prepare a tincture one of the filter bags is poured with boiled water, ingrained for 10-15 minutes, cooled to room temperature, after which it is taken 3 times a day.

A method for producing a diabetics prevention and maintenance therapy means is described in the Russian Federation patent 2002103852 for an invention (publ. Oct. 10, 2003) and comprises the steps of: extracting a fine cut mixture of plant material, including bean pods, repeatedly with water under heating, concentrating the combined extracts subsequently at a temperature of 38°-42° C. after separating the impurities, and drying them at 160°-170° C. at the dryer inlet and 70°-75° C. at the dryer outlet.

A method for producing a complex of biologically active compounds possessing a hypoglycaemic effect, is described in the Ukrainian patent 7005 for an invention (publ. Mar. 31, 1995) and comprises the steps of: performing the extraction of plant material with aqueous ethanol, evaporating and purifying the resulting product with ethanol followed by drying, wherein it is bean herb (*Phaseolus vulgaris* L.) that is subjected to extraction at a material:extractant ratio of 1:2.5-1:3, the resulting extract being evaporated to 1/10-1/11 of the initial volume.

The closest prior art of the method as claimed is a method for producing agents exhibiting hypoglycaemic activity described in the Ukrainian patent 48031 for an invention (publ. Aug. 15, 2002) and comprising the extraction of golden gram herb with 50% ethanol at a material to extractant ratio of 1:8-1:10, the resulting extract being concentrated to 1/18-1/20 of the initial volume, and after cleaning with alcohol the aqueous residue being treated with methylene chloride.

Among the main draw backs of the cited prior arts one should consider their complexity, duration, and considerable labour intensity, as well as the use of extracting agents hazardous to human health in the course of their implementing. Additionally, it should be noted that the primitivity of the described prior art methods for extracting the biologically active substances such as the plant material heat treatment with hot or boiling water, followed by maceration, causes decomposition of biologically active substances, thus reducing the implementation efficiency of the target product produced according to the methods.

The object of the invention is to develop a cost-effective method for producing a complex of biologically active substances with a high hypoglycaemic activity level, wherein the implementation of the method would enable to simplify and shorten the production process, as well as to reduce the complexity thereof.

DETAILED DESCRIPTION OF THE INVENTION

The problem is solved due to a method developed for producing a complex of biologically active substances exhibiting hypoglycaemic activity comprising the steps of extracting bean herb with alcohol followed by concentrating and/or drying the extract, wherein the extraction is carried out with 96% alcohol resulting in a first extract and a bean herb residue, wherein the first extract is concentrated resulting in a first solid extract or it is concentrated and dried resulting in a first dry extract, and the bean herb residue is extracted with 70% alcohol resulting in a second extract at least a portion of which being concentrated resulting in a second solid extract or being concentrated and dried resulting in a second dry extract.

The technical effect of the method implementation is enabling to prepare a complex of biologically active substances exhibiting a high level of hypoglycaemic activity; ensuring the material use efficiency; simplifying and shortening the production process, as well as reducing the complexity thereof. The technical effect is caused by the fact that upon implementing the method a complex of products rather than one target product can be obtained at a time, wherein their preparation is carried out by extracting, concentrating and drying without carrying out further purifications and other associated operations. Unlike the prior arts, the method provides extracting the maximum amount of biologically active substances due to the complete depletion of the materials (bean herb).

It is preferred such an embodiment of the invention, in which prior to the extraction the bean herb is fine cut by rolling into particles sized up to 1 mm. Rolling the bean herb (pods, stems, leaves) into particles of this size provides extracting maximum of useful agents in the course of the subsequent extractions, minimum of which being left in the residue (the cake). As a result when carrying out the sequential extractions with 96% and 70% alcohol a substantially complete depletion of the bean herb is achieved.

It is preferred such an embodiment of the invention, where at least a portion of the second extract is used as one of the target products—the liquid extract.

Thus, in accordance with the above description of the method when implemented it is possible to obtain five target products: a first solid extract, a first dry extract, a second solid extract, a second dry extract, and a liquid extract.

The first solid extract is lipophilic and has a viscous consistency, while it is obtained by extracting bean herb with 96% alcohol for three hours, followed by concentrating the resulting first extract under vacuum. The hypoglycaemic activity of this target product makes 59.8% per 24 hours.

The first dry extract is lipophilic and has a loose consistency. This target product is obtained by extracting bean herb with 96% alcohol for three hours resulting in a first extract, by concentrating the resulting first extract under vacuum resulting in a first solid extract, and drying the first solid extract resulting in a first dry extract. The hypoglycaemic activity of this target product makes 61.3% per 24 hours.

The second solid extract is hydrophilic and has a viscous consistency, while it is obtained by successive extracting bean herb first with 96% alcohol and then with 70% alcohol resulting in a second extract, being subsequently concentrated under vacuum. The hypoglycaemic activity of this target product makes 72.5% per 24 hours.

It should be noted that the second extract can also be used as a hydrophilic target product. According to its composition and consistency the second extract is a 70% tincture.

The second dry extract is hydrophilic and has a loose consistency. This target product is obtained by successive extracting bean herb first with 96% alcohol and then with 70% alcohol resulting in a second extract, by concentrating the second extract under vacuum resulting in a second solid extract, and its subsequent drying. The hypoglycaemic activity of this target product makes 75.5% per 24 hours.

The liquid extract is a hydrophilic compound obtained by extraction with 70% alcohol of the material, remained after extraction with 96% alcohol in the course of three to four hours. The hypoglycaemic activity of this target product makes 25.3% 24 per 24 hours.

The target products obtained in the course of the process can be further utilized, for example in the form of tablets, capsules, suppositories, ointments, gels, creams, wherein the target products are obtained without the use of substances hazardous to human health (e.g., methylene chloride).

It is preferred such an embodiment of the invention, in which 96% alcohol extraction is carried out with 5 volumes of extraction yield per mass unit of bean herb in the course of three hours. Thus, the ratio of the plant material to the extractant for the extraction is 1:5.

It is preferred such an embodiment of the invention, in which 70% alcohol extraction is carried out with 5 volumes of extraction yield per mass unit of bean herb in the course of three to four hours. Thus, the ratio of the plant material to the extractant for 70% alcohol extraction is 1:5.

The extractant (96% and 70% alcohol) concentration, the sequence of the extraction steps and their duration as well as the ratio of the plant material to the extractant are determined experimentally and scientifically justified and provide the complex extraction of bioactive compounds of various nature with virtually complete depletion of the bean herb. The resulting compounds provide the necessary level and range of the target products specific activity. Thus, the extraction with 96% alcohol followed by further concentrating or concentrating and drying results in obtaining lipophilic compounds (a first solid extract, a first dry extract) and when followed by further residue extraction with 70% alcohol along with concentrating or concentrating and drying, as a result hydrophilic compounds (a second solid extract, a second dry extract and a liquid extract) are obtained.

An exemplary embodiment of the method for producing biologically active substances with hypoglycaemic activity is described below.

The dry plant material, in particular bean herb (pods, stems, leaves) is fine cut by rolling into particles sized up to 1 mm. 20 kg of the fine cut plant material is fed to an extraction unit and extracted with 96% alcohol for three hours resulting in 5 volumes of a first extract and a material residue. The resulting first extract is concentrated under vacuum resulting in a first solid extract or concentrated and dried resulting in a first dry extract.

The bean herb residue extracted with 96% alcohol is then extracted with 70% alcohol in the course of three to four hours resulting in 5 volumes of a second extract (70% tincture), at least a part of which is then concentrated under vacuum resulting in a second solid extract or concentrated and dried resulting in a second dry extract. If necessary, at least part of the second extract is utilized to prepare a liquid extract.

The embodiment of the method as behind is cited exclusively by way of example in no way limiting other possible embodiments thereof.

Thus, it has been developed a method for producing biologically active substances possessing hypoglycaemic activity, wherein the implementation of the method enables to simplify and shorten the production process, as well as to reduce the complexity thereof. Moreover, the method as developed provides a complex of biologically active substances with a high level of hypoglycaemic activity along with the known active compounds of plant origin.

The invention claimed is:

1. A method for producing a number of biologically active substances exhibiting hypoglycaemic activity, comprising
extracting pods, stems and leaves of a *Phaseolus* bean plant with alcohol followed by concentrating or concentrating and drying the extract,
characterized in that the extraction is carried out with 96% alcohol resulting in a first lipophilic extract and a residue of the pods, stems and leaves of the *Phaseolus* bean plant, wherein
at least a portion of the first lipophilic extract is concentrated resulting in a first solid lipophilic extract or
it is concentrated and dried resulting in a first dry lipophilic extract,
and the residue of the pods, stems and leaves of the *Phaseolus* bean plant is extracted with 70% alcohol resulting in a second hydrophilic extract, at least a portion of which being concentrated resulting in a second solid hydrophilic extract or
being concentrated and dried resulting in a second dry hydrophilic extract, or
being used as a liquid hydrophilic extract.

2. The method of claim 1, characterized in that the pods, stems and leaves of a *Phaseolus* bean plant are fine cut prior to the extraction.

3. The method of claim 2, characterized in that the pods, stems and leaves of a *Phaseolus* bean plant are fine cut by rolling into particles sized up to 1 mm.

4. The method of claim 1, characterized in that 96% alcohol extraction is carried out with 5 volumes of extraction yield per mass unit of the pods, stems and leaves of the *Phaseolus* bean plant in the course of three hours.

5. The method of claim 1, characterized in that 70% alcohol extraction is carried out with 5 volumes of extraction yield per mass unit of the pods, stems and leaves of the *Phaseolus* bean plant in the course of three to four hours.

\* \* \* \* \*